United States Patent [19]

Murakami et al.

[11] Patent Number: 5,891,659
[45] Date of Patent: Apr. 6, 1999

[54] BIOLUMINESCENT ADENOSINE PHOSPHATE ESTER ASSAY AND REAGENT

[75] Inventors: Seiji Murakami; Tatsuya Sakakibara; Naoki Eisaki; Motoo Nakajima, all of Noda; Kazuhiro Imai, Tokyo, all of Japan

[73] Assignee: Kikkoman Corporation, Noda, Japan

[21] Appl. No.: 805,613

[22] Filed: Feb. 26, 1997

[30] Foreign Application Priority Data

Mar. 4, 1996 [JP] Japan ................................ 8-070911

[51] Int. Cl.[6] ............................................. C12Q 1/66
[52] U.S. Cl. .................... 435/8; 435/15; 435/21
[58] Field of Search .......................... 435/8, 4, 15, 17, 435/21, 25, 26, 92

[56] References Cited

U.S. PATENT DOCUMENTS 4,246,340  1/1981  Lundin et al. ............................. 435/8
4,960,696 10/1990  Imahori et al. ........................... 435/42

OTHER PUBLICATIONS

Database WPI, AN 88–318 079, Derwent Publications Ltd., London; & JP–A–63 223 799 (Eisai Co., Ltd.) 1988.
Soviet Patents Abstracts, B section, week 8805, 1985, Aug. 30, Derwent Publications Ltd., London., & SU–A–1317 027 (Moscow Lomonosov Univ).

Primary Examiner—Ralph Gitomer
Attorney, Agent, or Firm—Banner & Witcoff, Ltd.

[57] ABSTRACT

There is provided a bioluminescence reagent comprising at least pyruvate orthophosphate dikinase, phosphoenolpyruvic acid, pyrophosphoric acid, magnesium ion or another metallic ions, luciferin and luciferase, which reagent is such that the amount of luminescence is maintained in a high level and moreover stably without decaying for a long time in a bioluminescence reaction, and there is provided a method for quantitatively determining an adenosine phosphate ester or a substance taking part in the ATP conversion reaction in high sensitivity and high accuracy using an inexpensive and simple measuring apparatus.

7 Claims, 5 Drawing Sheets

FIG. 2

STANDARD CURVE OF AMP
(10 MINUTES AFTER THE START OF REACTION)

FIG. 4

STANDARD CURVE OF ATP
( 10 MINUTES AFTER THE START OF REACTION )

BIOLUMINESCENT ADENOSINE PHOSPHATE ESTER ASSAY AND REAGENT

BACKGROUND OF THE INVENTION

1. Field of the Invention

This invention relates to a bioluminescence reagent that the amount of luminescence may be maintained in a high level and moreover stably without decaying for a long time in a bioluminescence method, a method for quantitatively determining an adenosine phosphate ester using the reagent, and a method for quantitatively determining a substance taking part in an ATP conversion reaction system using the reagent.

The ATP conversion reaction system in the invention means any reaction system which is composed, for example of a combination of enzymes and substrates, and wherein ATP is formed or consumed at the time of reaction.

For example, it includes, so far known ATP assaying systems each utilizing a bioluminescence reaction (a reaction system wherein luciferase is made to act on ATP, luciferin, dissolved oxygen and magnesium ion to form AMP, pyrophosphoric acid, oxyluciferin, carbon dioxide and light), and an assaying system for an adenosine phosphate ester such as AMP is, ADP, ATP or cyclic AMP disclosed in the invention, and in addition a reaction system wherein another reaction system is combined with such an assay system (reaction system) and in the reaction system after the combination, ATP is formed or consumed at the time of reaction.

2. Description of the Related Prior Art

Heretofore, there has been known an ATP-quantitatively determining method by a so-called bioluminescent method wherein a bioluminescence reagent comprising luciferin, luciferase and magnesium ions (or other metallic ions) is reacted with a sample containing adenosine triphosphate (hereinafter referred to as ATP) and the amount of luminescence formed is quantitatively determined.

However, although this method has an advantage that ATP can be determined quickly, it has a disadvantage that the stability of luminescence is poor, and more specifically luminescence fades out in a very short time, and therefore it has a problem that for securing sensitivity and accuracy, it gets necessary to control the reaction time strictly and use a luminometer, a measuring apparatus equipped with an auto-injection function for capturing luminescence fading out in a short time.

Heretofore, some techniques for stabilizing luminescence over a long time in this bioluminescence method have been developed, but any of them has problems to be improved.

Namely, in a method which comprises adding coenzyme A (hereinafter abbreviated as CoA) to a reaction system (Patent Kohyo No. 6-500921), a luciferase-luciferin reaction is carried out in the presence of CoA, under a condition of lowering the peak intensity of light formed in the reaction, by a small amount (for example, by about 3 to 30% of the peak intensity under the absence of this condition), and thereby all the amount of light emitted in the reaction (i.e., amount measured by integrating the curve of intensity to time) is increased, and thereby all the light output can be measured more simply and more accurately.

However, in this method, it is compelled to lower the peak (sensitivity) of light formed by the reaction, and the relations between the intensity of luminescence and time get to be curve relations, and the amount of luminescence gradually decays. Therefore, it cannot be expected to maintain the amount of luminescence at a high level stably for a long time.

Further, since a thiol reagent has a SH group on the structure, it, in general, is easily oxidized and has a problem on storage as a solution. Further, since CoA on the market is one extracted from a yeast or the like, it is expensive, and moreover a possibility that ATP, etc. are mixed is noted. The inclusion of ATP is not desired because it causes the increase of the background when ATP is an object to be assayed.

In a method which comprises adding pyrophosphoric acid to the reaction system at the time when a bioluminescence reaction progressed in some extent and the amount of luminescence started to lower, and thereby forming intense luminescence momentarily (Arch. Biochem. Biophys. 46, 399–416; 1955), the peak intensity of light is increased again in the middle of the luminescence reaction and thereby the extension of the luminescence time is attempted, but it is impossible to stabilize luminescence over a long time.

In a method which comprises using, in a bioluminescence method, a D-luciferin analog in the reaction system as a competitive inhibitor (Patent Kokai No. 55-13893), although the amount of luminescence can be maintained at a certain level and stably for a long time, the intensity of luminescence is suppressed or inhibited by at least 25%, particularly 50 to 90% by the addition of the inhibitor, and thus the method has a drawback that the lowering of sensitivity is compelled.

In a method which comprises using a polyphosphoric acid compound and a sulfhydryl compound together in a bioluminescence method (Patent Kokai No. 8-47399), the peak intensity of light formed in the luminescence reaction is increased and thereby the extension of the luminescence time is attempted, but it is impossible to maintain luminescence stably over a long time.

Further, as to the above bioluminescence methods, there is no regeneration of ATP in any of them, and they each have a drawback that luminescence decays with time lapse as ATP is consumed.

Therefore, for maintaining the amount of luminescence stably for a long time without decaying, it is compelled to examine the substrate concentrations, enzyme concentrations, pH, temperature, addition of a suppressor or inhibitor, etc., and even thereby sufficiently satisfactory results cannot be expected.

On the other hand, a quantitative determination method of cyclic AMP using a bioluminescence method shown by the following reaction formula is known.

Reaction Formula

Cyclic AMP $\xrightarrow[\text{(Reaction 1)}]{\text{Cyclic 3', 5'-nucleotide phosphodiesterase}}$ AMP AMP + ATP $\xrightarrow[\text{Mg}^{2+} \text{ (Reaction 2)}]{\text{Adenylate kinase}}$ 2ADP ADP + phosphoenol pyruvic acid $\xrightarrow[\text{Mg}^{2+} \text{ (Reaction 3)}]{\text{Pyruvate kinase}}$ Pyruvic acid + ATP -continued
Reaction Formula (Reaction 4)

This method is characterized by a method of quantitatively determining cyclic AMP by Reaction 1 wherein cyclic AMP is hydrolyzed with cyclic-3',5'-nucleotide phosphodiesterase to form AMP in the reaction system, Reaction 2 wherein the AMP is reacted with adenylate kinase in the presence of magnesium ion and a trace amount of ATP to convert it to ADP, Reaction 3 wherein the ADP is reacted with pyruvate kinase in the presence of magnesium ion and phosphoenolpyruvic acid to convert it to ATP and pyruvic acid, Reaction 4 wherein the ATP is reacted with luciferase in the presence of luciferin, magnesium ion (or other metallic ions) and dissolved oxygen to form luminescence, and measuring the amount of luminescence formed in Reaction 4 (METHODS IN ENZYMOLOGY 38, 62–65; 1974).

However, in this method, AMP formed from cyclic AMP is converted to ADP by the reaction with adenylate kinase in the presence of a trace amount of ATP, and the ADP is converted to ATP with pyruvate kinase, and therefore, it is required to add a trace amount of ATP in advance to the reaction system.

This additions of ATP is not desirable because when cyclic AMP is the object to be assayed, the ATP causes the increase of the background.

As a result, a blank value corresponding to cyclic AMP of at least $1.3 \times 10^{-9}$ M is formed, and thus the method has a problem that cyclic AMP cannot be determined with high sensitivity.

Thus the invention aims to provide a bioluminescence reagent that the amount of luminescence is maintained in a high level and moreover stably without decaying for a long time in a bioluminescence reaction, and provide a method for quantitatively determining an adenosine phosphate ester or a substance taking part in an ATP conversion reaction in high sensitivity and high accuracy using an inexpensive and simple measuring apparatus.

SUMMARY OF THE INVENTION

The present inventors have intensely made sequential researches to solve these problems, and they have found that when a reagent comprising ATP regenerating enzyme, substrates of ATP regenerating enzyme, magnesium ion, luciferin and luciferase is reacted with a sample containing an adenosine phosphate ester, the amount of luminescence is maintained in a high level and moreover stable without decaying for a long time, and it gets possible to quantitatively determine the adenosine phosphate ester in high sensitivity and high accuracy using an inexpensive and simple measuring apparatus wherein said ATP regenerating enzyme catalyzes the formation of ATP from AMP.

Thus the invention is (1) a bioluminescence reagent comprising ATP regenerating enzyme, substrates of ATP regenerating enzyme, magnesium ion or other metallic ions, luciferin and luciferase, the invention is also (2) a bioluminescence reagent comprising pyruvate orthophosphate dikinase, phosphoenolpyruvic acid, pyrophosphoric acid, magnesium ion or other metallic ions, luciferin and luciferase, the invention is also (3) a method for quantitatively determining an adenosine phosphate ester which comprises reacting the above bioluminescence reagent with a sample containing the adenosine phosphate ester, and measuring the amount of luminescence formed, the invention is also (4) a method for quantitatively determining ATP which comprises reacting the above bioluminescence reagent with a sample containing ATP, and measuring the amount of luminescence formed, the invention is also (5) a method for quantitatively determining AMP which comprises reacting the above bioluminescence reagent with a sample containing AMP, and measuring the amount of luminescence formed, the invention is also (6) a method for quantitatively determining ADP which comprises reacting a bioluminescence reagent comprising pyruvate orthophosphate dikinase, phosphoenolpyruvic acid, pyrophosphoric acid, magnesium ion or other metallic ions, luciferin, luciferase and pyruvate kinase with a sample containing ADP, and measuring the amount of luminescence formed, the invention is also (7) a method for quantitatively determining cyclic AMP which comprises reacting a bioluminescence reagent comprising pyruvate orthophosphate dikinase, phosphoenolpyruvic acid, pyrophosphoric acid, magnesium ion or other metallic ions, luciferin, luciferase and cyclic-3',5'-nucleotide phosphodiesterase with a sample containing cyclic AMP, and measuring the amount of luminescence formed, the invention is also (8) a method for quantitatively determining a substance taking part in an ATP conversion reaction system which comprises adding a bioluminescence reagent comprising pyruvate orthophosphate dikinase, phosphoenolpyruvic acid, pyrophosphoric acid, magnesium ion or other metallic ions, luciferin and luciferase to the ATP conversion reaction system to cause reaction, and measuring the amount of luminescence formed, and invention is also (9) a method for quantitatively determining pyruvate orthophosphate dikinase, phosphoenolpyruvic acid, pyrophosphoric acid, luciferin, luciferase, pyruvate kinase, acetate kinase, creatine kinase or cyclic-3',5'-nucleotide phosphodiesterase utilizing the above quantitatively determining method.

DETAILED DESCRIPTION OF THE PREFERRED EMBODIMENTS

First, the bioluminescence reagent used in the invention is prepared using as constituents at least pyruvate orthophosphate dikinase or phosphoenolpyruvate synthase or other ATP regenerating enzyme, substrates of ATP regenerating enzyme, magnesium ion or other metallic ions, luciferin and luciferase. For example, a bioluminescence reagent used in the invention is prepared using as constituents at least pyruvate orthophosphate dikinase, phosphoenolpyruvic acid, pyrophosphoric acid, magnesium ion or other metallic ions, luciferin and luciferase.

Among the above constituents of the bioluminescence reagent, pyruvate orthophosphate dikinase is a known enzyme catalyzing such a reaction that it acts on AMP, phosphoenolpyruvic acid and pyrophosphoric acid in the presence of magnesium ion to form ATP, pyruvic acid and phosphoric acid , and also catalyzing the reverse reaction thereof.

The physical properties and production process thereof are already known, and it is relatively easily available.

As the enzyme, those derived from plants and from microorganisms are known.

As those derived from plants, there can, for example, be mentioned enzymes from the leaves of corn [Biochemistry 12, 2862–2867 (1973)] and the leaves of sugarcane [The Biochemical Journal 114, 117–125 (1969)].

As those derived from microorganisms, there can, for example, be mentioned enzymes produced by microorganisms belonging to Propionibacterium shermanii [Biochemistry 10, 721–729 (1971)], Acetobacter xylinum [Journal of Bacteriology (1970)], Bacteroides symbiosus [Metoods in Enzymology 42, 199–212 (1975)] and the genus Microbispora (for example, Microbispora thermorosea IFO 14047), etc.

A specific example of production of the enzyme produced by a microorganism is shown below.

50 ml of a medium composed of 0.2% yeast extract, 0.2% Casamino acid, 0.001% ferrous sulfate, 0.05% potassium chloride, 0.1% dipotassium hydrogenphosphate, 0.05% magnesium sulfate and 0.3% lactic acid (pH 7.0) was put in a Sakaguchi flask (capacity: 500 ml), and sterilized at 121° C. for 15 minutes.

Microbispora thermorosea IFO 14047 was inoculated in the medium, and shaking cultured at 45° C. overnight to give a culture.

50 ml of this culture was inoculated in 1 L of a medium having the same composition as above in a 5-L Sakaguchi flask, and cultured overnight to give a culture.

500 ml portions of this culture were inoculated in 20 L of a medium having the same composition as above in each of two 30-L jar fermenters, respectively, and aeration stirring cultured at 45° C. for 24 hours under the conditions of an aeration rate of 20 L/min and a stirring rate of 300 r.p.m.

After the completion of the culture, the cells were collected from 40 L of this culture using Microsa (made by Asahi Chemical Industry Co., Ltd.). 20 mM HEPES buffer (pH 7.5) containing 5 mM EDTA, 1 mM MgSO4 and 1 mM DTT (hereinafter referred to as Buffer A) was added to part (200 g) of the cells, and the cells were sufficiently suspended to make the total volume 700 ml. Purification of the enzyme 700 ml of the above cell suspension was subjected to the operations of each stage shown below.

Step 1 (preparation of a crude enzyme solution)

8.75 g of lysozyme (made by Nagase Biochemical Industry Co.) was added to 700 ml of the above cell suspension, the mixture was left alone at room temperature for 2 hours with gentle stirring, 23.1 g of diammonium hydrogenphosphate was added, the mixture was stirred at room temperature for further 2 hours, and then the cells were fractured.

The fracture liquid was centrifuged at 7,000 r.p.m. for 15 minutes, and the supernatant part was collected whereby 620 ml of the liquid was obtained.

Step 2 (the first QAE-Sephadex chromatography)

Ammonium sulfate was dissolved in the above 620 ml solution at a rate of 2 g/100 ml, and the solution was put on about 700 ml of QAE-Sephadex previously equilibrated with the above Buffer A (pH 7.5) containing 0.15M ammonium sulfate to adsorb the enzyme. The resin (gel) was washed with the above Buffer A (pH 7.5) containing 0.15M ammonium sulfate to remove unabsorbed proteins, and then elution was carried out using the above Buffer A (pH 7.5) containing 0.6M ammonium sulfate.

Step 3 (the second QAE-Sephadex chromatography)

The eluate was concentrated and dialyzed against Buffer A (pH. 7.5) by a hollow fiber ultrafiltration apparatus (PAN 13-DX, made by Asahi Medical Co.), and then put on QAE-Sephadex column (diameter 6 cm ×15 cm) equilibrated in advance with the Buffer A (pH 7.5) to adsorb the enzyme. resin was washed with the Buffer A (pH 7.5) containing 0.15M ammonium sulfate to remove unabsorbed proteins, and then the enzyme was eluted by a linear concentration gradient using 1.5 L each of the Buffer A (pH 7.5) containing 0.15M ammonium sulfate and the Buffer A (pH 7.5) containing 0.8M ammonium sulfate.

Step 4 (Butyl-Toyopearl chromatography)

The active fractions were recovered, ammonium sulfate was added to adjust the ammonium sulfate concentration to 1M, and the mixture was put on Butyl-Toyopearl (made by Toso Co., Ltd.) column (diameter 4.5 cm×15 cm) equilibrated with Buffer A (H 7.5) contained 1M ammonium sulfate to adsorb the enzyme.

The enzyme was eluted with a linear gradient of an ammonium sulfate concentration (1.0M~0 M) in 1.2 L of the Buffer A.

Step 5 (gel filtration chromatography)

The active fractions were concentrated to 2 ml using an ultrafiltration membrane apparatus made by Amicon Co. (cut-off: 10,000), and 100 $\mu$l of the concentrate was put on TSK G 3000 SWX1 (diameter 0.76 cm ×30 cm ×2) equilibrated in advance with 20 mM HEPES buffer (pH 7.5) containing 0.3M ammonium sulfate, whereby gel filtration was carried out.

The whole enzyme was subjected to gel filtration and the active fraction were concentrated. The concentrate was subjected again to the same column operations as above to carry out gel filtration. The whole enzyme was subjected to the gel filtration, and 5.4 ml of the active fraction eluted were collected.

The above fraction showed the single protein band on SDS-polyacrylamide gel electrophoresis and contained 6.65 mg protein with a specific activity of 9.92 U/mg.

Assay method of pyruvate orthophosphate dikinase activity.

(Method to determine ATP formed by a luminescence method)

180$\mu$l of 50 mM BIS-TRIS PROPANE buffer (pH 6.8) containing 3 mM magnesium sulfate, 25 mM ammonium sulfate, 2 mM 2-mercaptoethanol, 2 mM pyrophosphoric acid, 2 mM phosphoenolpyruvic acid and 0.1 mM AMP, preincubated at 37° C., was pipetted into a microtube, and 20 $\mu$l of an enzyme solution having a appropriate activity was added to carry out reaction for 15 minutes, and the reaction solution was boiled for 3 minutes in boiling water to cease the reaction. The reaction solution was diluted suitably, 50 $\mu$l of the dilution was put in a test tube, 50 $\mu$l of "Lucifer LU" (made by KIKKOMAN CORPORATION) solution was added dropwise, and then the amount of luminescence was measured. Separately, a graph was prepared in advance by examining the relations between the concentration of ATP and the amount of luminescence using ATP standard solutions having known concentrations. The umol of ATP formed per minute at 37° C. was calculated using this graph, and this value is assumed to be the activity unit in the enzyme solution used. The amount of enzyme which forms 1 μmol of ATP per minute at 37° C. is defined to be 1 unit (U).

Preferred concentration ranges of the constituents of the bioluminescence reagent of the invention are shown below.

(a) pyruvate orthophosphate dikinase; a concentration of 0.001 U/ml (final concentration) or more, particularly 0.002 to 100 U/ml (final concentration).

(b) phosphoenolpyruvic acid; a concentration of 0.1 mM (final concentration) or more, particularly 0.5 to 8.0 mM (final concentration).

(c) pyrophosphoric acid; a concentration of 1.0 μM (final concentration) or more, particularly 5.0 to 100 μM (final concentration).

(d) magnesium ion; a concentration of 1.0 mM (final concentration) or more, particularly 5.0 to 100 mM (final concentration).

(e) luciferin; a concentration of 5.0 μM (final concentration) or more, particularly 50.0 to 10,000 μM (final concentration).

(f) luciferase; a concentration of 0.1 mg/ml (final concentration) or more, particularly 0.5 to 20 mg/ml (final concentration).

(g) ammonium sulfate; a concentration of 0.1 mM (final concentration) or more, particularly 0.5 to 100 mM (final concentration).

(h) dithiothreitol; a concentration of 0.1 mM (final concentration) or more, particularly 0.5 to 10 mM (final concentration).

(i) EDTA; a concentration of 0.1 mM (final concentration) or more, particularly 0.5 to 10 mM (final concentration).

(j) HEPES buffer (pH 7.0); a concentration of 10 mM (final concentration) or more, particularly 20 to 200 mM (final concentration).

(k) cyclic-3',5'-nucleotide phosphodiesterase; a concentration of 0.01 U/ml (final concentration) or more, particularly 0.02 to 10 U/ml (final concentration).

(l) pyruvate kinase; a concentration of 0.01 U/ml (final concentration) or more, particularly 0.02 to 10 U/ml (final concentration).

As luciferase used herein, any luciferase used in ATP assay by luciferin-luciferase systems may be used.

For example, there can be mentioned luciferases derived from Luciola cruciata, Luciola lateralis, American firefly, etc., these luciferases produced by genetic recombination methods, etc.

As buffers, there can further be used Tris-succinic acid buffer, BIS-Tris PROPANE buffer, MES buffer, etc.

As preferred concentration, the same concentration range as in the above HEPES buffer can be mentioned, and as preferred pH range, 6.5 to 8.0 can be mentioned.

Various compounds may be added to the bioluminescence reagent of the invention to effect the enzymatic reaction and luminescence reaction smoothly.

As such compounds, there can, for example, be mentioned stabilizers, surfactants, activators, etc.

Namely, among the above constituents, (g) ammonium sulfate is used as an activator of pyruvate orthophosphate dikinase, (h) dithiothreitol and (i) EDTA as stabilizers of luciferase, and (j) HEPES buffer (pH 7.0) as a stabilizer of the reaction system, and they are not essential components.

Description is made below on the mechanisms of the invention.

The method for determination of AMP according to the invention can be shown by the following reaction formula.

In the above reaction, as shown in the broken line frame, a reaction (a) to make pyruvate orthophosphate dikinase act on AMP, pyrophosphoric acid, phosphoenolpyruvic acid and magnesium ion and thereby form ATP, pyruvic acid and phosphoric acid is carried out, and then, as shown in the alternate long and short dash line frame, a reaction (b) to make luciferase act on ATP, luciferin, dissolved oxygen and magnesium ion and thereby form AMP, oxyluciferin, carbon dioxide and light is carried out.

Thus, the determination of AMP is carried out by combining Reaction (a) and Reaction (b) to form an ATP conversion reaction system and measuring the amount of luminescence formed.

Description is made below on the main points of this reaction.

First, AMP is converted to ATP by Reaction (a), and then by Reaction (b) ATP is consumed to form luminescence and AMP, and this AMP is subjected to Reaction (a) to regenerate ATP.

This ATP is subjected again to Reaction (b) to consume ATP and cause luminescence.

Thereafter, these two reactions occur simultaneously, continuously and repeatedly.

It is confirmed that luminescence formed by this series of the ATP conversion reaction system is stable over 10 minutes or more in a high level without decaying, and still stable after the time lapse of 5 hours almost without decaying.

Next, description is made on the method for determination of ATP according to the invention.

The method for determination of ATP of the invention can be represented by the same reaction formula as in the above method for determination of AMP.

In this reaction, first ATP is consumed by Reaction (b) to cause luminescence and form AMP, this AMP formed is converted to ATP by Reaction (a), and this ATP regenerated is then subjected again to Reaction (b) to consume ATP and cause luminescence.

Thereafter, these two reactions occur simultaneously, continuously and repeatedly.

Luminescence formed in the ATP conversion reaction system of the invention is stable over at least minutes or more in a high level without decaying, and still stable after the time lapse of 5 hours almost without decaying.

Next, description is made on the method for determination of cyclic AMP according to the invention.

This determination method can be represented by the following reaction formula.

This determination method is characterized in that an ATP conversion reaction system is constituted by combining another reaction (c) to hydrolyze cyclic AMP with cyclic-3',5'-nucleotide phosphodiesterase and thereby form AMP, shown in the alternative long and two short dashes line frame, with Reaction (a) (as shown above) and Reaction (b) (as shown above).

In the above reaction, first, as shown in the alternative long and two short dashes line frame, Reaction (c) to hydrolyze cyclic AMP with cyclic-3',5'-nucleotide phosphodiesterase to form AMP is carried out and thereby cyclic AMP is converted to AMP, then by Reaction (a) AMP is converted to ATP, and then by Reaction (b) ATP is consumed to cause luminescence and form AMP. This AMP is converted to ATP by Reaction (a). This ATP regenerated is subjected again to Reaction (b) to consume ATP and cause luminescence.

Thereafter, these two reactions occur simultaneously, continuously and repeatedly.

Luminescence formed in the ATP conversion reaction system is stable over at least 10 minutes or more in a high level without decaying, and still stable after the time lapse of 5 hours almost without decaying.

Next, description is made on the method for determination of ADP according to the invention.

This determination method can be represented by the following reaction formula.

This determination method is characterized in that another reaction (d) to react ADP with pyruvate kinase in the presence of magnesium ion and phosphoenolpyruvic acid to form ATP and pyruvic acid, shown in the alternative long and three short dashes line frame, is combined with Reaction (a) (as shown above) and Reaction (b) (as shown above).

In this connection, acetate kinase or creatine kinase may be used in place of pyruvate kinase used.

In the above reaction, first, as shown in the alternative long and three short dashes line frame, Reaction (d) to react ADP with pyruvate kinase in the presence of magnesium ion and phosphoenolpyruvic acid and thereby form ATP and pyruvic acid is carried out, thereby ADP is converted to ATP, then by Reaction (b) this ATP is consumed to cause luminescence and form AMP, and then by Reaction (a) this AMP is converted again to ATP. This ATP is subjected again to Reaction (b), to ATP is consumed, luminescence occurs and ATP is converted to AMP.

Thereafter, these two reactions occur simultaneously, continuously and repeatedly.

Luminescence formed in this series of ATP conversion reaction system is stable over at least 10 minutes or more in a high level without decaying, and still stable after the time lapse of 5 hours almost without decaying.

Since luminescence is formed exactly depending on (directly proportional to) the concentration of any of a series of the enzymes and substrates taking part in the above ATP conversion reaction systems, it is possible to determine a substance taking part in the ATP conversion reactions such as any of the enzymes and substrates in high sensitivity and high accuracy and moreover in a short time by measuring the amount of luminescence.

Thus, according to the invention, it is possible to determine many substances taking part in ATP conversion reaction systems, for example, adenosine phosphate esters such as AMP, ADP, ATP and cyclic AMP, pyruvate orthophosphate dikinase, phosphoenolpyruvic acid, pyrophosphoric acid, luciferin, luciferase, pyruvate kinase, acetate kinase, creatine kinase, cyclic-3',5'-nucleotide phosphodiesterase, etc. in high sensitivity and high accuracy and moreover in a short time.

EXAMPLE 1

(Preparation of a bioluminescence reagent for AMP determination)

The substances mentioned in the following (a) to (j) were dissolved in ultra-pure water so that the concentration thereof could be the respective final concentrations, whereby a bioluminescence reagent for AMP determination was prepared.

| (a) pyruvate orthophosphate dikinase (final concentration) (the preparation process is as described above) | 0.4 U/ml | |
|---|---|---|
| (b) phosphoenolpyruvic acid (made by Boehringer-Mannheim GmbH) | 4.2 mM | (final concentration) |
| (c) pyrophosphoric acid | 42 $\mu$M | (final concentration) |
| (d) magnesium ion | 15 mM | (final concentration) |
| (e) luciferin (made by Sigma Co.) | 1.5 mM | (final concentration) |
| (f) luciferase (made by KIKKOMAN CORPORATION) | 1.4 mg/ml | (final concentration) |
| (g) ammonium sulfate | 7.5 mM | (final concentration) |
| (h) dithiothreitol | 1.0 mM | (final concentration) |
| (i) EDTA | 1.0 mM | (final concentration) |
| (j) HEPES buffer (pH 7.0) | 50 mM | (final concentration) |

In the above, (g) ammonium sulfate is used to strengthen the activation of pyruvate orthophosphate dikinase, (h) dithiothreitol and (i) EDTA to stabilize luciferase and (j) HEPES buffer (pH 7.0) to stabilize the reaction system.

EXAMPLE 2
(Method for determination of AMP)

100 $\mu$l of the bioluminescence reagent prepared in Example 1 and 100 $\mu$l of each of samples containing AMP in several concentrations (standard solutions) were reacted, and the amount of luminescence formed was measured by Lumat LB 9501, luminometer made by Berthold Co. to carry out the determination of AMP.

The measurement of the amount of luminescence was carried out by a method to measure the amount of luminescence per one second at intervals of 20 seconds over 10 minutes after the start of the reaction.

Figure 1:
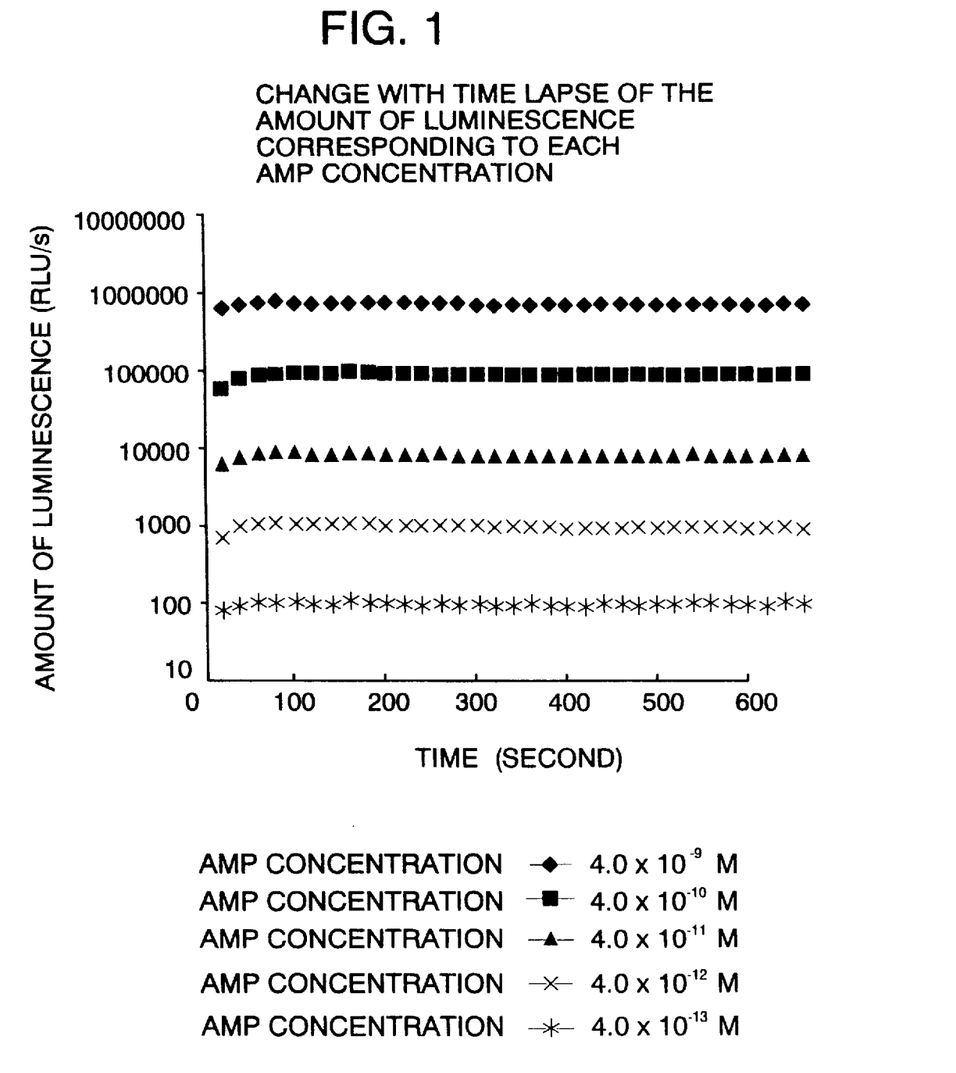
FIG. 1 shows the change with time lapse of the amount of luminescence corresponding to each AMP concentration. The axis of ordinate shows the amount of luminescence (RLU/s) and the axis of abscissa shows time (second).

The change with time lapse of the amount of luminescence corresponding to each AMP concentration was examined, and the results were shown in FIG. 1.

Figure 2:
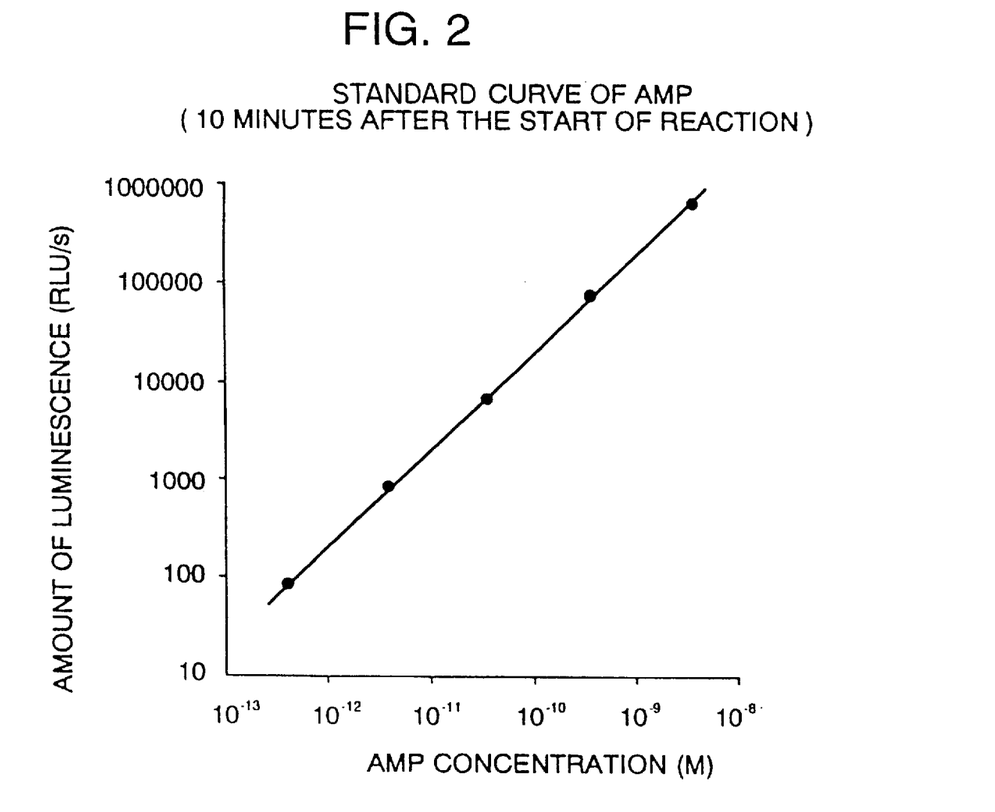
FIG. 2 shows a standard curve showing the relations between the AMP concentration and the amount of luminescence (at 10 minutes after the start of the reaction). The axis of ordinate shows the amount of luminescence (RLU/s) and the axis of abscissa shows the AMP concentration (M).

Further, the relations between the AMP concentration and the amount of luminescence (value at 10 minutes after the start of the reaction) were examined, and the results were shown in FIG. 2 as an AMP calibration curve.

It is understood from the results of FIG. 1 that according to the invention, in the method for determination of AMP utilizing the bioluminescence reaction, the amount of luminescence is stable in a high level and moreover without decaying for a long time.

Further, it is understood from the results of FIG. 2 that according to the invention, $10^{-8}$ to $10^{-13}$M of AMP can be determined in extremely high sensitivity and high accuracy.

EXAMPLE 3
(Preparation of a bioluminescence reagent for ATP determination)

The substances mentioned in the following (a) to (j) were dissolved in ultra-pure water so that the concentrations thereof could be the respective final concentrations, whereby a bioluminescence reagent for ATP determination was prepared.

| (a) pyruvate orthophosphate dikinase (final concentration) | 0.4 U/ml | |
|---|---|---|
| (b) phosphoenolpyruvic acid (made by Boehringer-Mannheim GmbH) | 4.2 mM | (final concentration) |
| (c) pyrophosphoric acid | 42 mM | (final concentration) |
| (d) magnesium ion | 15 mM | (final concentration) |
| (e) luciferin (made by Sigma Co.) | 1.5 mM | (final concentration) |
| (f) luciferase (made by KIKKOMAN CORPORATION) | 1.4 mg/ml | (final concentration) |
| (g) ammonium sulfate | 7.5 mM | (final concentration) |
| (h) dithiothreitol | 1.0 mM | (final concentration) |
| (i) EDTA | 1.0 mM | (final concentration) |
| (j) HEPES buffer (pH 7.0) | 50 mM | (final concentration) |

In the above, (g) ammonium sulfate is used to strengthen the activation of pyruvate orthophosphate dikinase, (h) dithiothreitol and (i) EDTA to stabilize luciferase and (j) HEPES buffer (pH 7.0) to stabilize the reaction system.

EXAMPLE 4
(Method for determination of ATP)

100 $\mu$l of the bioluminescence reagent prepared in Example 3 and 100 $\mu$l of each of samples containing ATP in several concentrations (standard solutions) were reacted, and the amount of luminescence formed was measured by Lumat LB 9501, luminometer made by Berthold Co. to carry out the determination of ATP.

The measurement of the amount of luminescence was carried out by a method to measure the amount of luminescence per one second at intervals of 20 seconds over 10 minutes after the start of the reaction.

Figure 3:
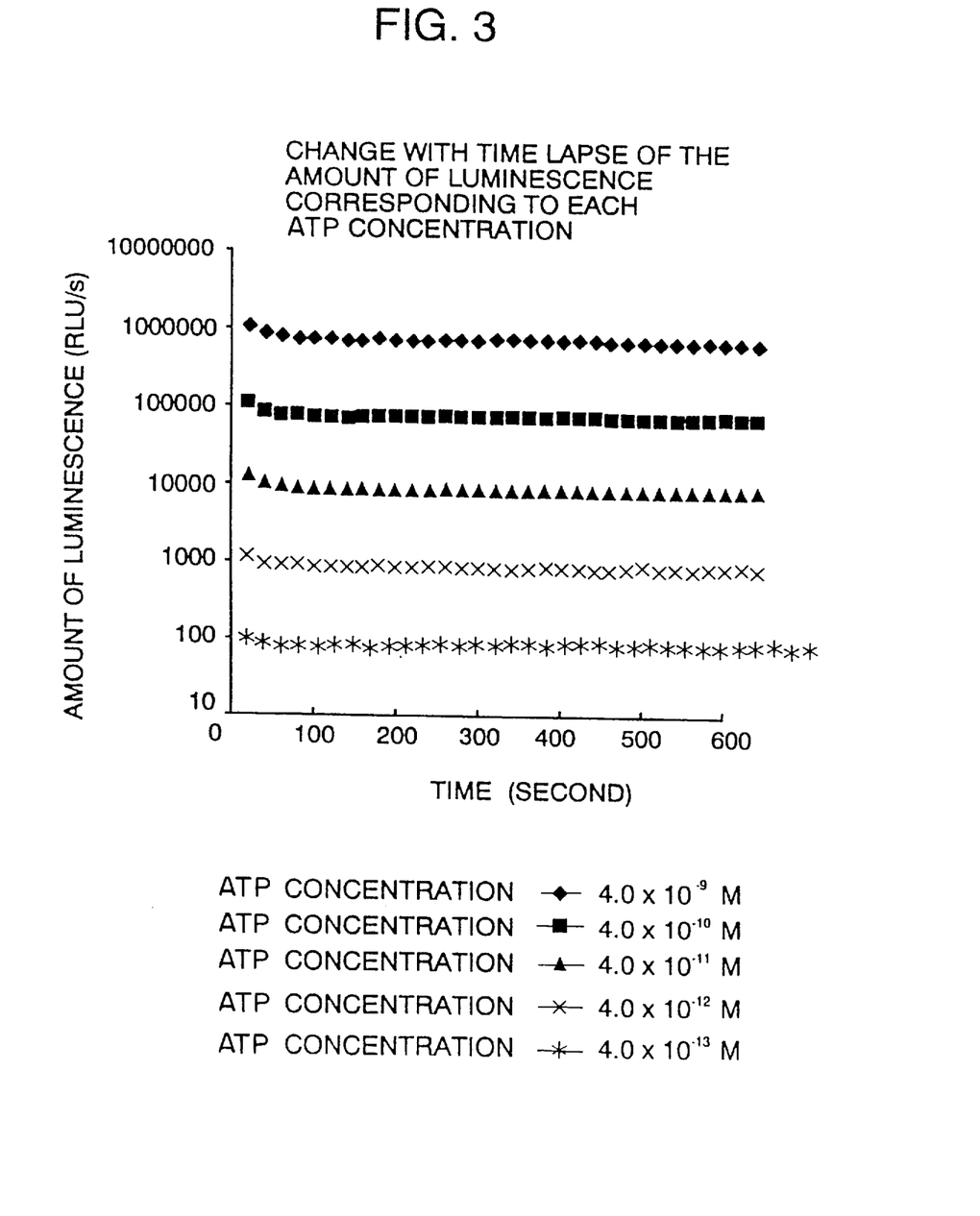
FIG. 3 shows the change with time lapse of the amount of luminescence corresponding to each ATP concentration. The axis of ordinate shows the amount of luminescence (RLU/s) and the axis of abscissa shows time (second).

The change with time lapse of the amount of luminescence corresponding to each ATP concentration was examined, and the results were shown in FIG. 3.

Figure 4:
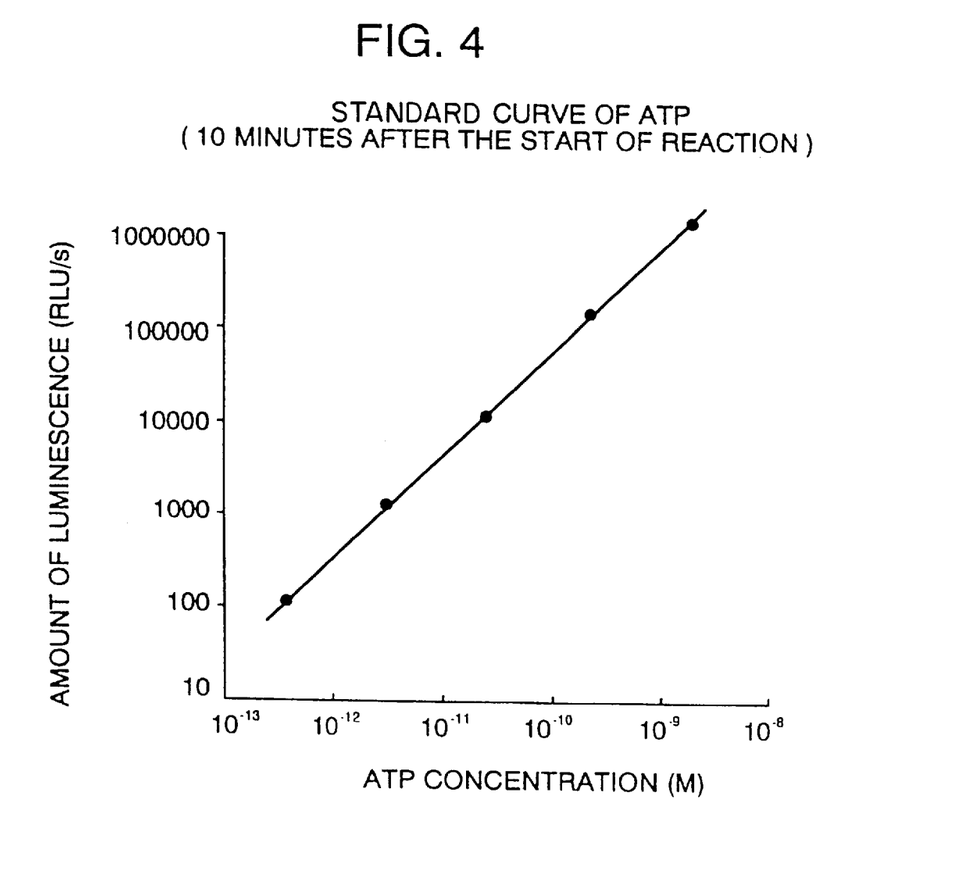
FIG. 4 shows a standard curve showing the relations between the ATP concentration and the amount of luminescence (at 10 minutes after the start of the reaction). The axis of ordinate shows the amount of luminescence (RLU/s) and the axis of abscissa shows the ATP concentration (M).

Further, the relations between the ATP concentration and the amount of luminescence (value at 10 minutes after the start of the reaction) were examined, and the results were shown in FIG. 4 as an ATP calibration curve.

It is understood from the results of FIG. 3 that according to the invention, in the method for determination of ATP utilizing the bioluminescence reaction, the amount of luminescence is stable in a high level and moreover without decaying for a long time.

Further, it is understood from the results of FIG. 4 that according to the invention, $10^{-8}$ to $10^{-13}$M of ATP can be determined in high sensitivity and high accuracy.

EXAMPLE 5
(Preparation of a bioluminescence reagent for ADP determination)

The substances mentioned in the following (a) to (k) were dissolved in ultra-pure water so that the concentrations thereof could be the respective final concentrations, whereby a bioluminescence reagent for ADP determination was prepared.

| (a) pyruvate orthophosphate dikinase (final concentration) (the preparation process is as described above) | 0.4 U/ml | |
|---|---|---|
| (b) phosphoenolpyruvic acid (made by Boehringer-Mannheim GmbH) | 4.2 mM | (final concentration) |
| (c) pyrophosphoric acid | 42 $\mu$M | (final concentration) |
| (d) magnesium ion | 15 mM | (final concentration) |
| (e) luciferin | 1.5 mM | (final concentration) |

-continued

| | | |
|---|---|---|
| (made by Sigma Co.) | | |
| (f) luciferase | 1.4 mg/ml | (final concentration) |
| (made by KIKKOMAN CORPORATION) | | |
| (g) ammonium sulfate | 7.5 mM | (final concentration) |
| (h) dithiothreitol | 1.0 mM | (final concentration) |
| (i) EDTA | 1.0 mM | (final concentration) |
| (j) HEPES buffer (pH 7.0) | 50 mM | (final concentration) |
| (k) pyruvate kinase (made by Boehringer-Mannheim GmbH) | 0.4 U/ml | (final concentration) |

EXAMPLE 6
(Preparation of a bioluminescence reagent for cyclic AMP determination)

The substances mentioned in the following (a) to (k) were dissolved in ultra-pure water so that the concentrations thereof could be the respective final concentrations, whereby a bioluminescence reagent for cyclic AMP determination was prepared.

| | | |
|---|---|---|
| (a) pyruvate orthophosphate dikinase (final concentration) (the preparation process is as described above) | 0.4 U/ml | |
| (b) phosphoenolpyruvic acid (made by Boehringer-Mannheim GmbH) | 4.2 mM | (final concentration) |
| (c) pyrophosphoric acid | 42 $\mu$M | (final concentration) |
| (d) magnesium ion | 15 mM | (final concentration) |
| (e) luciferin (made by Sigma Co.) | 1.5 mM | (final concentration) |
| (f) luciferase (made by KIKKOMAN CORPORATION) | 1.4 mg/ml | (final concentration) |
| (g) ammonium sulfate | 7.5 mM | (final concentration) |
| (h) dithiothreitol | 1.0 mM | (final concentration) |
| (i) EDTA | 1.0 mM | (final concentration) |
| (j) HEPES buffer (pH 7.0) | 50 mM | (final concentration) |
| (k) cyclic-3',5'-nucleotide phosphodiesterase (made by Sigma Co.) | 0.4 U/ml | (final concentration) |

EXAMPLE 7
(Method for determination of ATP)

100 $\mu$l of the bioluminescence reagent for ATP determination prepared in Example 3 and 100 $\mu$l of a sample containing ATP in a concentration of $1.0 \times 10^{10}$M (final concentration) (a standard solution) were reacted, and the amount of luminescence formed was measured by Lumat LB 9501, luminometer made by Berthold Co., and thereby the change of luminescence with time lapse was examined.

The measurement of the amount of luminescence was carried out by a method to measure the amount of luminescence per one second at intervals of one second over 10 minutes after the start of the reaction.

For comparison, the same operations as in the above method for determination of ATP were carried out to determine ATP except that (a) pyruvate orthophosphate dikinase was not used.

Figure 5:
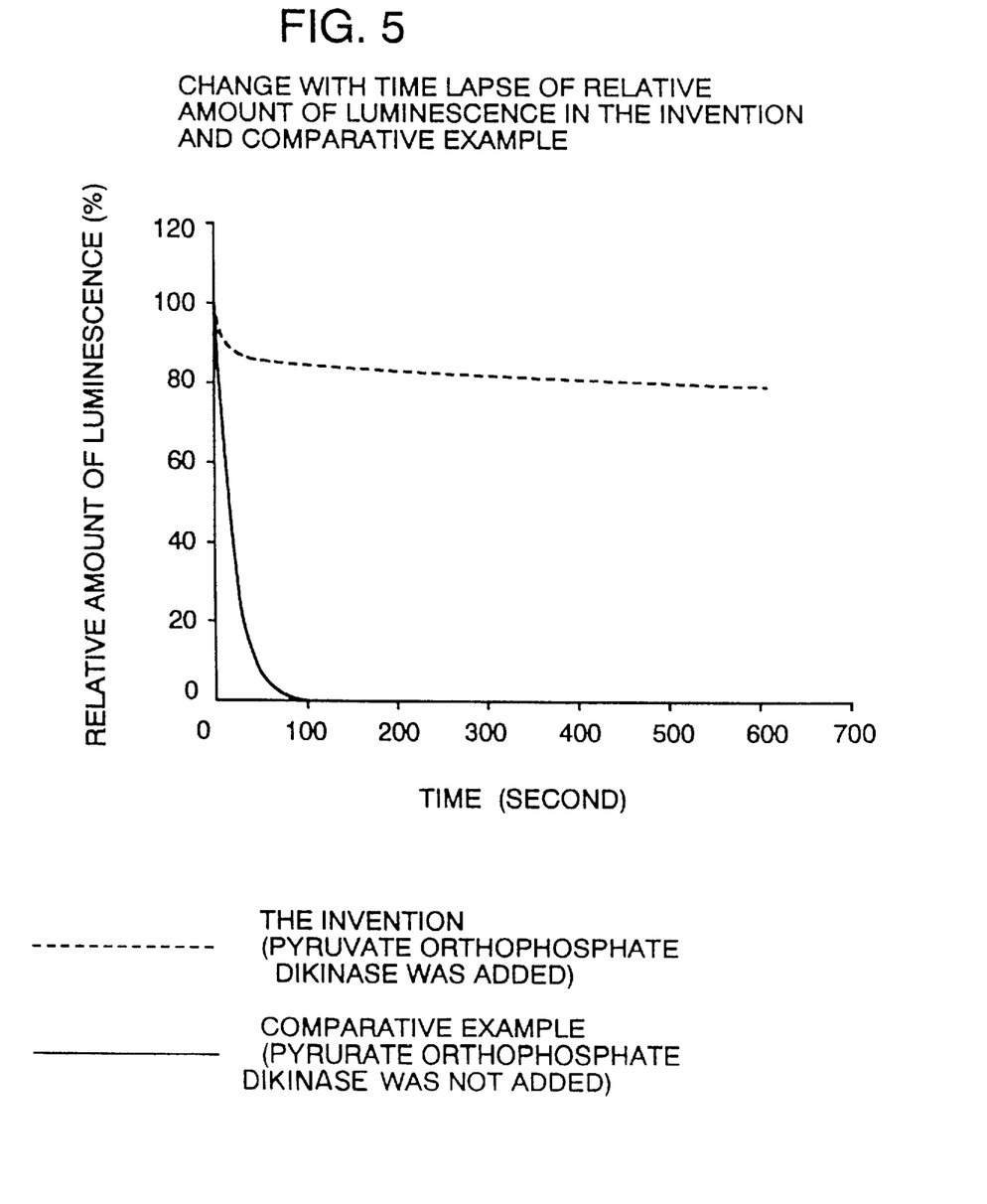
FIG. 5 shows the change with time lapse of the relative amount of luminescence in the case where the ATP concentration is $1.0 \times 10^{-10}$ M.

The results are shown in FIG. 5.

As apparent from the results of FIG. 5, in the case of the method for determination of ATP where pyruvate orthophosphate dikinase was not used (continuous line; the method of the comparative example), the amount of luminescence reaches the peak extremely rapidly, namely a flash of light is emitted, and then luminescence decays rapidly (100 seconds later becoming $\frac{1}{100}$, 200 seconds later becoming $\frac{1}{1,000}$). Therefore, it will be understood that for measuring the rapid flash at the initial stage of the reaction, particularly immediately after the start of the reaction, an injection method for quickly mixing a sample containing ATP with the bioluminescence reagent, work requiring special trouble or a delicate measuring apparatus such as a luminometer gets necessary.

On the other hand, it will be understood that in the method for determination of ATP of the invention using pyruvate orthophosphate dikinase (shown by the broken line), the amount of luminescence is maintained in a high level and stably for a long time (10 minutes) without decaying.

Therefore, it will be understood that according to the invention, since a condition very excellent for the continuous analysis of an ATP conversion reaction is given, and the amount of luminescence measured by integrating the locus of the intensity of luminescence to time is remarkably increased compared with the comparative example, determination in high sensitivity and high accuracy gets possible using an inexpensive and simple measuring apparatus.

Further, it will be understood from the results of FIG. 1 to FIG. 5 obtained in the above Example 2, 4 and 7 that since luminescence is formed extremely exactly depending on (directly proportional to) the concentration of any of a series of the enzymes and substrates taking part in the ATP conversion reaction systems, it is possible to determine a substance taking part in the ATP conversion reaction such as any of the enzymes and substrates in high sensitivity and high accuracy and moreover in a short time by measuring the amount of luminescence. Namely, it will be understood that if the bioluminescence reagent of the invention is used, it is possible to determine any of many substances taking part in the ATP conversion reaction systems, for example, adenosine phosphate esters such as AMP, ADP, ATP and and cyclic AMP, pyruvate orthophosphate dikinase, phosphoenolpyruvic acid, pyrophosphoric acid, luciferin, luciferase, pyruvate kinase, acetate kinase, creatine kinase, cyclic-3',5'-nucleotide phosphodiesterase, etc. in high sensitivity and high accuracy and moreover in a short time.

Further, it will also be understood that the bioluminescence reagent of the invention can be utilized preferably in the assay of adenosine phosphate esters such as ATP, and substances and enzymes taking part in ATP conversion reaction systems in clinical chemistry, clinical microbiology, biochemical research, biological research and bioenergetics.

What is claimed is:

1. A bioluminescence reagent comprising:
    (a) ATP regenerating enzyme which catalyzes the formation of ATP from AMP,
    (b) substrates of ATP regenerating enzyme,
    (c) magnesium ion or another divalent metallic cation,
    (d) luciferin and
    (e) luciferase.

2. A bioluminescence reagent comprising:
    (a) pyruvate orthophosphate dikinase,
    (b) phosphoenolpyruvic acid,
    (c) pyrophosphoric acid,
    (d) magnesium ion or another divalent metallic cations,
    (e) luciferin and
    (f) luciferase.

3. A method for quantitatively determining an adenosine phosphate ester which comprises reacting a bioluminescence reagent comprising:

(a) pyruvate orthophosphate dikinase,
(b) phosphoenolpyruvic acid,
(c) pyrophosphoric acid,
(d) magnesium ion or another divalent metallic cation,
(e) luciferin and
(f) luciferase with a sample containing the adenosine phosphate ester, measuring the amount of luminescence formed and then quantitatively determining an amount of the adenosine phosphate ester with a standard curve obtained by using an adenosine phosphate ester standard solution having a predetermined concentration.

4. The method according to claim 3 which comprises reacting a bioluminescence reagent comprising:

(a) pyruvate orthophosphate dikinase,
(b) phosphoenolpyruvic acid,
(c) pyrophosphoric acid,
(d) magnesium ion or another divalent metallic cation,
(e) luciferin and
(f) luciferase with a sample containing ATP, and measuring the amount of luminescence formed to determine ATP quantitatively.

5. The method according to claim 3 which comprises reacting a bioluminescence reagent comprising:

(a) pyruvate orthophosphate dikinase,
(b) phosphoenolpyruvic acid,
(c) pyrophosphoric acid,
(d) magnesium ion or another divalent metallic cation,
(e) luciferin and
(f) luciferase with a sample containing AMP, and measuring the amount of luminescence formed to determine AMP quantitatively.

6. The method according to claim 3 which comprises reacting a bioluminescence reagent comprising:

(a) pyruvate orthophosphate dikinase,
(b) phosphoenolpyruvic acid,
(c) pyrophosphoric acid,
(d) magnesium ion or other divalent metallic cation,
(e) luciferin,
(f) luciferase and
(g) pyruvate kinase with a sample containing ADP, and measuring the amount of luminescence formed to determine ADP quantitatively.

7. The method according to claim 3 which comprises reacting a bioluminescence reagent comprising:

(a) pyruvate orthophosphate dikinase,
(b) phosphoenolpyruvic acid,
(c) pyrophosphoric acid,
(d) magnesium ion or another divalent metallic cation,
(e) luciferin,
(f) luciferase and
(g) cyclic-3',5'-nucleotide phosphodiesterase with a sample containing cyclic AMP, and measuring the amount of luminescence formed to determine cyclic AMP quantitatively.

* * * * *